(12) United States Patent
Knopp (10) Patent No.: US 7,637,740 B2
(45) Date of Patent: Dec. 29, 2009

(54) SYSTEMS AND METHODS FOR TEMPORALLY STAGING TEETH

(75) Inventor: Peter G. Knopp, Palo Alto, CA (US)

(73) Assignee: Align Technology, Inc., Santa Clara, CA (US)

( * ) Notice: Subject to any disclaimer, the term of this patent is extended or adjusted under 35 U.S.C. 154(b) by 196 days.

(21) Appl. No.: 10/788,555

(22) Filed: Feb. 27, 2004

(65) Prior Publication Data

US 2005/0191593 A1    Sep. 1, 2005

(51) Int. Cl.
*A61C 3/00* (2006.01)
(52) U.S. Cl. ............................................. 433/24
(58) Field of Classification Search .................. 433/24, 433/6
See application file for complete search history.

(56) References Cited

U.S. PATENT DOCUMENTS 5,975,893 A * 11/1999 Chishti et al. .................. 433/6
2005/0244782 A1 * 11/2005 Chishti et al. ................. 433/24

OTHER PUBLICATIONS

Histomorhometric Study of aleveolar bone turnover in Orthodontic Tooth Movement www.ncbi.nln.nihgov/entrez/—King GJ, Keeling SD, Wronski TJ, Bone. 1991; 12(6): 401-9. Department Of Orthodontics, University of Florida, College of Dentistry Gainesville 32610.

Alveolar Bone Turnover and Tooth Movement in Male Rats After Removal of Orthodontic Appliances www.ncbi.nln.nihgov/entrez/—King GJ, Latta L, Rutenberg J, Ossi A, Keeling SD, AM J Orthod Dentofacial Orthop. Mar. 1997;111(3):266-75 Department Of Orthodontics, University of Florida, College of Dentistry Gainesville 32610.

Source: Contemporary Orthodontics $3^{rd}$ Edition, Profitt, William R., P. 303.

* cited by examiner

*Primary Examiner*—John J Wilson
*Assistant Examiner*—Heidi M Eide
(74) *Attorney, Agent, or Firm*—Brooks, Cameron & Huebsch, PLLC (57) ABSTRACT

Systems and methods are disclosed for moving teeth by moving a first tooth; and moving a second tooth while isolating the first tooth at a rest position.

15 Claims, 9 Drawing Sheets

SYSTEMS AND METHODS FOR TEMPORALLY STAGING TEETH

BACKGROUND

The present invention is related generally to the field of orthodontics, and more particularly to a system and a method for gradually repositioning teeth.

A fundamental objective in orthodontics is to realign a patient's teeth to positions where the teeth function optimally and aesthetically. Typically, appliances such as braces are applied to the teeth of the patient by a treating orthodontist. Each appliance exerts continual forces on the teeth which gradually urge the teeth toward their ideal positions. Over a period of time, the orthodontist adjusts the appliances to move the teeth toward their final destination.

The process of attaching the braces to teeth is tedious and painful. Additionally, each visit to the orthodontist is time consuming and expensive. The process is further complicated by uncertainties in determining a final arrangement for each tooth. Generally, the final tooth arrangement is determined by the treating orthodontist who writes a prescription. Traditionally, the prescription is based on the orthodontist's knowledge and expertise in selecting the intended final position of each tooth and without a precise calculation of forces being exerted on the teeth when they contact each other.

SUMMARY

In one aspect, systems and methods are disclosed for moving teeth by moving a first tooth; and moving a second tooth while isolating the first tooth at a rest position.

In another aspect, a system to treat teeth includes means for moving a first tooth; and means for moving a second tooth while isolating the first tooth at a rest position.

In another aspect, a system for generating one or more appliances for a patient includes a processor; a display device coupled to the processor; a data storage device coupled to the processor; a scanner coupled to the processor for providing data to model the patient's masticatory system; means for moving a first tooth; means for moving a second tooth while isolating the first tooth at a rest position; and a dental appliance fabrication machine coupled to the processor for generating the appliances in accordance with the moved tooth and the isolated tooth.

Implementations of each of the above aspects may include one or more of the following. The second tooth can be moved for a first duration and immobilized for a second duration. The duration can be on an hourly basis, a daily basis, or a weekly basis. A plurality of appliances can be generated, wherein the appliances comprise polymeric shells having cavities and wherein the cavities of successive shells have different geometries shaped to receive and resiliently reposition the teeth from one arrangement to a successive arrangement. A first cavity isolates the first tooth at the rest position. A second cavity urges the second tooth to one of the successive position. The appliance can be replaced on an intra-day basis, daily basis, multi-day basis, intra-week basis, or weekly basis. Additionally, the system can move a first group of teeth; and move a second group of teeth while isolating the first group of teeth at a rest position. Each group can be contiguous teeth or can be non-contiguous teeth.

Advantages of the invention include one or more of the following. Tooth movement can be achieved quickly. Other advantages include moving the teeth in a manner that is optimum in methodology. The system also provides the ability to stop moving certain teeth that have reached their intended locations while allowing other teeth to move. The prescription may be automatically interpreted in order to generate an image as well as a digital data set representing the final tooth arrangement.

DESCRIPTION

Figure 1:
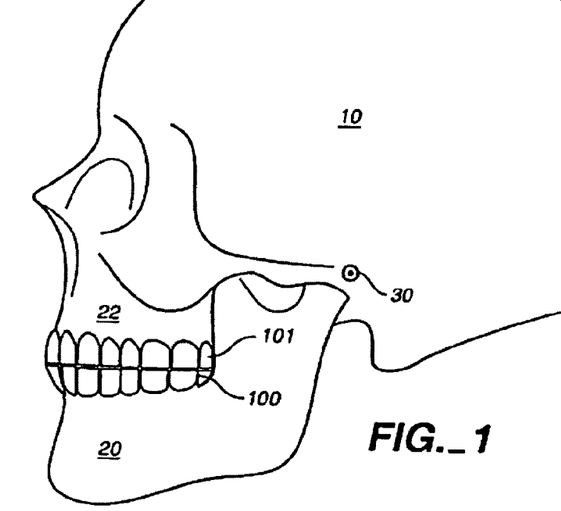
FIG. 1 is an elevational diagram showing the anatomical relationship of the jaws of a patient.

FIG. 1 shows a skull 10 with an upper jaw bone 22 and a lower jaw bone 20. The lower jaw bone 20 hinges at a joint 30 to the skull 10. The joint 30 is called a temporomandibular joint (TMJ). The upper jaw bone 22 is associated with an upper jaw 101, while the lower jaw bone 20 is associated with a lower jaw 100.

A computer model of the jaws 100 and 101 is generated, and a computer simulation models interactions among the teeth on the jaws 100 and 101. The computer simulation allows the system to focus on motions involving contacts between teeth mounted on the jaws.

The computer simulation allows the system to render realistic jaw movements which are physically correct when the jaws 100 and 101 contact each other. The model of the jaw places the individual teeth in a treated position. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions are applied to one jaw, but may also be applied to both jaws. Based on the occlusion determination, the final position of the teeth can be ascertained.

Figure 2A:
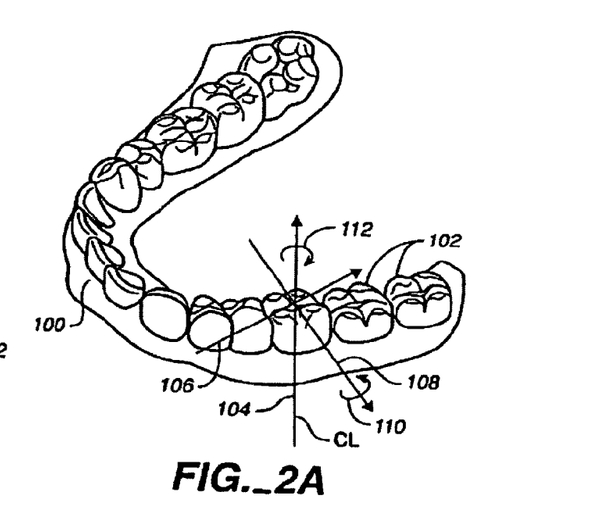
FIG. 2A illustrates in more detail the patient's lower jaw and provides a general indication of how teeth may be moved by the methods and apparatus of the present invention.

Referring now to FIG. 2A, the lowerjaw 100 includes a plurality of teeth 102, for example. At least some of these teeth may be moved from an initial tooth arrangement to a final tooth arrangement. As a frame of reference describing how a tooth may be moved, an arbitrary centerline (CL) may be drawn through the toot 102. With reference to this centerline (CL), each tooth may be moved in orthogonal directions represented by axes 104, 106, and 108 (where 104 is the centerline). The tooth 102 may be rotated about the axis 108 (root angulation) and the axis 104 (torque) as indicated by arrows 110 and 112, respectively. Additionally, the tooth may be rotated about the axis 106. Thus, all possible free-form motions of the tooth can be performed.

Figure 2B:
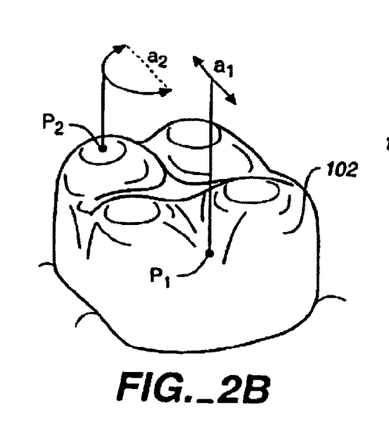
FIG. 2B illustrates a single tooth from FIG. 2A and defines how tooth movement distances are determined.

FIG. 2B shows how the magnitude of any tooth movement may be defined in terms of a maximum linear translation of any point P on a tooth 102. Each point $P_1$ will undergo a cumulative translation as that tooth is moved in any of the orthogonal or rotational directions defined in FIG. 2A. That is, while the point will usually follow a nonlinear path, there is a linear distance between any point in the tooth when determined at any two times during the treatment. Thus, an arbitrary point $P_1$ may in fact undergo a true side-to-side translation as indicated by arrow $d_1$, while a second arbitration point $P_2$ may travel along an arcuate path, resulting in a final translation $d_2$. Many aspects of the present invention are defined in terms of the maximum permissible movement of a point $P_1$ induced on any particular tooth. Such maximum tooth movement, in turn, is defined as the maximum linear translation of that point $P_1$ on the tooth which undergoes the maximum movement for that tooth in any treatment step.

Figure 2C:
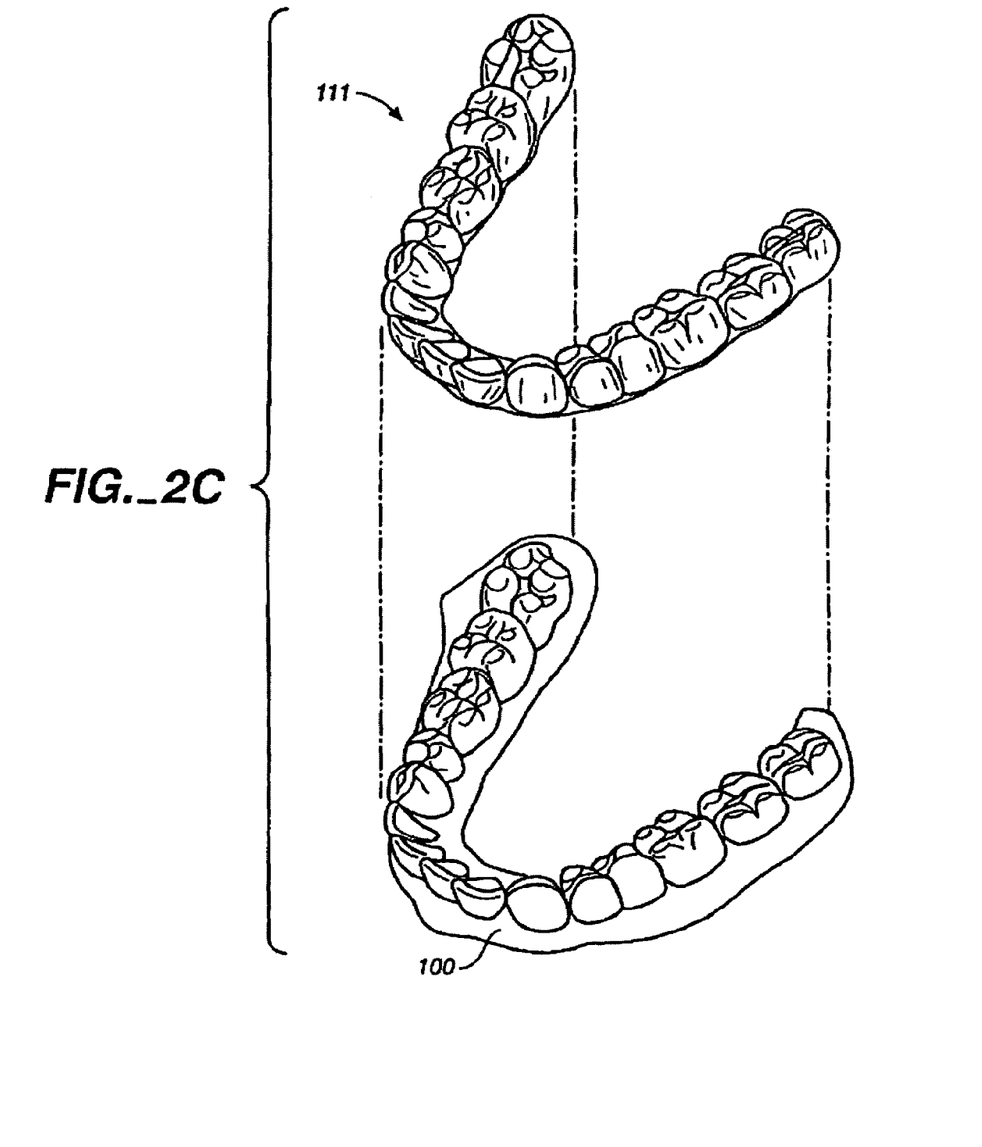
FIG. 2C illustrates the jaw of FIG. 2A together with an incremental position adjustment appliance which has been configured according to the methods and apparatus of the present invention.

FIG. 2C shows one adjustment appliance 111 which is worn by the patient in order to achieve an incremental repositioning of individual teeth in the jaw as described generally above. The appliance is a polymeric shell having a teeth receiving cavity. This is described in U.S. application Ser. No. 09/169,036, filed Oct. 8, 1998, which claims priority from U.S. application Ser. No. 08/947,080, filed Oct. 8, 1997, which in turn claims priority from provisional application No. 06/050,352, filed Jun. 20, 1997 (collectively the "prior applications"), the full disclosures of which are incorporated by reference.

As set forth in the prior applications, each polymeric shell may be configured so that its tooth receiving cavity has a geometry corresponding to an intermediate or final tooth arrangement intended for the appliance. The patient's teeth are repositioned from their initial tooth arrangement to a final tooth arrangement by placing a series of incremental position adjustment appliances over the patient's teeth. The adjustment appliances are generated at the beginning of the treatment, and the patient wears each appliance until the pressure of each appliance on the teeth can no longer be felt. At that point, the patient replaces the current adjustment appliance with the next adjustment appliance in the series until no more appliances remain. Conveniently, the appliances are generally not affixed to the teeth and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such overcorrection may be desirable in order to offset potential relapse after the repositioning method has been terminated, i.e., to permit some movement of individual teeth back toward their precorrected positions. Overcorrection may also be beneficial to speed the rate of correction, i.e., by having an appliance with a geometry that is positioned beyond a desired intermediate or final position; the individual teeth will be shifted toward the position at a greater rate. In such cases, the use of an appliance can be terminated before the teeth reach the positions defined by the appliance.

The polymeric shell 111 can fit over all teeth present in the upper or lower jaw. Often, only certain one(s) of the teeth will be repositioned while others of the teeth will provide a base or an anchor region for holding the appliance 111 in place as the appliance 111 applies a resilient repositioning force against the tooth or teeth to be repositioned. In complex cases, however, multiple teeth may be repositioned at some point during the treatment. In such cases, the teeth which are moved can also serve as a base or anchor region for holding the repositioning appliance.

The polymeric appliance 111 of FIG. 2C may be formed from a thin sheet of a suitable elastomeric polymer, such as Tru-Tain 0.03 in, thermal forming dental material, available from Tru-Tain Plastics, Rochester, Minn. Usually, no wires or other means will be provided for holding the appliance in place over the teeth. In some cases, however, it will be desirable or necessary to provide individual anchors on teeth with corresponding receptacles or apertures in the appliance 100 so that the appliance can apply an upward force on the tooth which would not be possible in the absence of such an anchor.

Figure 3:
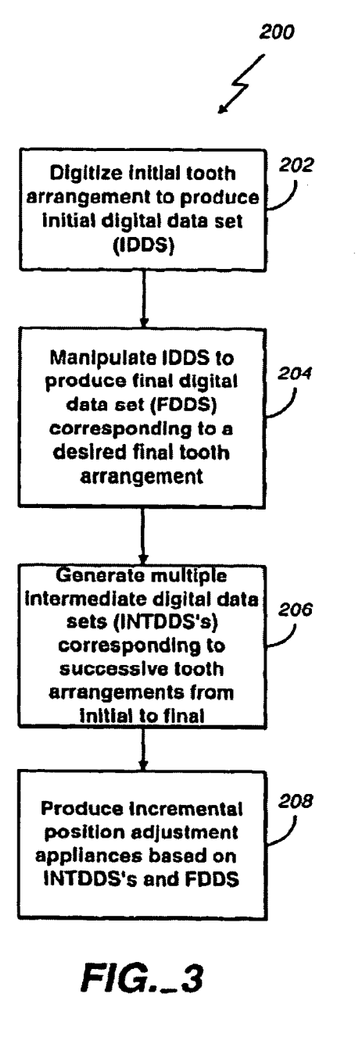
FIG. 3 is a block diagram illustrating a process for producing incremental position adjustment appliances.

FIG. 3 shows a process 200 for producing the incremental position adjustment appliances for subsequent use by a patient to reposition the patient's teeth. As a first step, an initial digital data set (IDDS) representing an initial tooth arrangement is obtained (202). The IDDS may be obtained in a variety of ways. For example, the patient's teeth may be scanned or imaged using X-rays, three dimensional X-rays, computer-aided tomographic images or data sets, or magnetic resonance images, among others. The teeth data may be generated by a destructive scanner, as described in the incorporated-by-reference U.S. application Ser. No. 09/169,034, filed Oct. 8, 1998.

The IDDS is then manipulated using a computer having a suitable graphical user interface (GUI) and software appropriate for viewing and modifying the images. More specific aspects of this process will be described in detail below.

Individual tooth and other components may be segmented or isolated in the model to permit their individual repositioning or removal from the digital model. After segmenting or isolating the components, the user will often reposition the tooth in the model by following a prescription or other written specification provided by the treating professional. Alternatively, the user may reposition one or more teeth based on a visual appearance or based on rules and algorithms programmed into the computer. Once the user is satisfied, the final teeth arrangement is incorporated into a final digital data set (FDDS) (204). The FDDS is used to generate appliances that move the teeth in a specified sequence. First, the centers of each tooth model may be aligned using a number of methods. One method is a standard arch. Then, the teeth models are rotated until their roots are in the proper vertical position. Next, the teeth models are rotated around their vertical axis into the proper orientation. The teeth models are then observed from the side, and translated vertically into their proper vertical position. Finally, the two arches are placed together, and the teeth models moved slightly to ensure that the upper and lower arches properly mesh together. The meshing of the upper and lower arches together is visualized using a collision detection process to highlight the contacting points of the teeth.

Based on both the IDDS and the FDDS, a plurality of intermediate digital data sets (INTDDSs) are defined to correspond to incrementally adjusted appliances (206). Finally, a set of incremental position adjustment appliances are produced based on the INTDDs and the FDDS (208).

In 204, final positions for the upper and lower teeth in a masticatory system of a patient are determined by generating a computer representation of the masticatory system. An occlusion of the upper and lower teeth is computed from the computer representation; and a functional occlusion is computed based on interactions in the computer representation of the masticatory system. The occlusion may be determined by generating a set of ideal models of the teeth. Each ideal model in the set of ideal models is an abstract model of idealized teeth placement which is customized to the patient's teeth, as discussed below. After applying the ideal model to the computer representation, and the position of the teeth is optimized to fit the ideal model. The ideal model may be specified by one or more arch forms, or may be specified using various features associated with the teeth.

Figure 4:
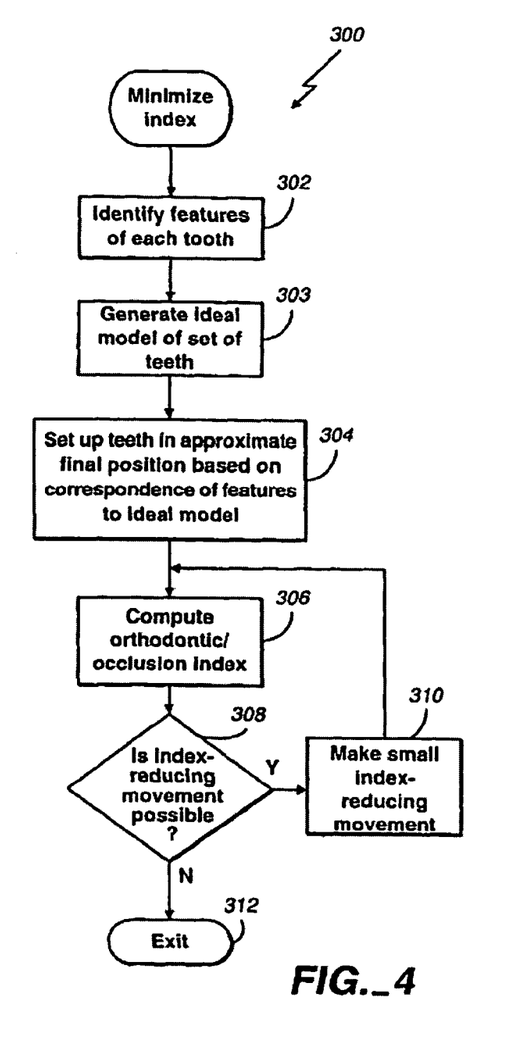
FIG. 4 is a flow chart illustrating a process for optimizing a final placement of the patient's teeth.

FIG. 4 illustrates a process 300 which optimizes the final placement of the teeth based on teeth features. First, the process 300 automatically or, with human assistance, identifies various features associated with each tooth to arrive at a model of the teeth (302). An ideal model set of teeth is then generated either from casts of the patient's teeth or from patients with a good occlusion (303).

From (302), the process 300 positions the model of the teeth in its approximate final position based on a correspondence of features to the ideal model (304). In that step, each tooth model is moved so that its features are aligned to the features of a corresponding tooth in the ideal model. The features may be based on cusps, fossae, ridges, distance-based metrics, or shape-based metrics. Shape-based metrics may be expressed as a function of the patient's arches, among others.

For example, cusp features associated with each tooth may be used. Cusps are pointed projections on the chewing surface of a tooth. In a detection stage, a possible cusp is viewed as an "island" on the surface of the tooth, with the candidate cusp at the highest point on the island. "Highest" is measured with respect to the coordinate system of the model, but could just as easily be measured with respect to the local coordinate system of each tooth. The set of all possible cusps is determined by looking for all local maxima on the tooth model that are within a specified distance of the top of the bounding box of the model. First, the highest point on the model is designated as the first candidate cusp. A plane is passed through this point, perpendicular to the direction along which the height of a point is measured. The plane is then lowered by a small predetermined distance along the Z axis. Next, all vertices connected to the tooth and which are above the plane and on some connected component are associated with the candidate cusp as cusps. This step is also referred to as a flood fill step. From each candidate cusp point, outward flooding is performed, marking each vertex on the model visited in this matter as part of the corresponding candidate cusp. After the flood fill step is complete, every vertex on the model is examined. Any vertex that is above the plane and has not been visited by one of the flood fills is added to the list of candidate cusps. These steps are repeated until the plane is traveled a specified distance.

After the detection stage, the cusp detection process may include a rejection stage where local geometries around each of the cusp candidates are analyzed to determine if they possess non-cusp-like features. Cusp candidates that exhibit non-cusp-like features are removed from the list of cusp candidates. Various criteria may be used to identify non-cusp-like features. According to one test, the local curvature of the surface around the cusp candidate is used to determine whether the candidate possesses non-cusp-like features. Alternatively, a measure of smoothness is computed based on the average normal in an area around the candidate cusp. If the average normal deviates from the normal at the cusp by more than a specified amount, the candidate cusp is rejected.

Next, the process 300 computes an orthodontic/occlusion index (306). One index which may be used is the PAR (Peer Assessment Rating) index. In addition to PAR, other metrics such as shape-based metrics or distance-based metrics may be used.

The PAR index identifies how far a tooth is from a good occlusion. A score is assigned to various occlusal traits which make up a malocclusion. The individual scores are summed to obtain an overall total, representing the degree a case deviates from normal alignment and occlusion. Normal occlusion and alignment is defined as all anatomical contact points being adjacent, with a good intercuspal mesh between upper and lower buccal teeth, and with nonexcessive overjet and overbite.

In PAR, a score of zero would indicate good alignment, and higher scores would indicate increased levels of irregularity. The overall score is recorded on pre- and posttreatment dental casts. The difference between these scores represents the degree of improvement as a result of orthodontic intervention and active treatment. The eleven components of the PAR Index are: upper right segment; upper anterior segment; upper left segment; lower right segment; lower anterior segment; lower left segment; right buccal occlusion; overjet; overbite; centerline; and left buccal occlusion. In addition to the PAR index, other indices may be based on distances of the features on the tooth from their ideal positions or ideal shapes.

From 306, the process 300 determines whether additional index-reducing movements are possible (308). Here, all possible movements are attempted, including small movements along each major axis as well as small movements with minor rotations. An index value is computed after each small movement and the movement with the best result is selected. In this context, the best result is the result that minimizes one or more metrics such as PAR-based metrics, shape-based metrics or distance-based metrics. The optimization may use a number of techniques, including simulated annealing technique, hill climbing technique, best-first technique, Powell method, and heuristics technique, among others. Simulated annealing techniques may be used where the index is temporarily increased so that another path in the search space with a lower minimum may be found. However, by starting with the teeth in an almost ideal position, any decrease in the index should converge to the best result.

In 308, if the index can be optimized by moving the tooth, incremental index-reducing movement inputs are added (310) and the process loops back to (306) to continue computing the orthodontic/occlusion index. Alternatively, in the event that the index cannot be optimized any more, the process 300 exits (312).

Figure 5:
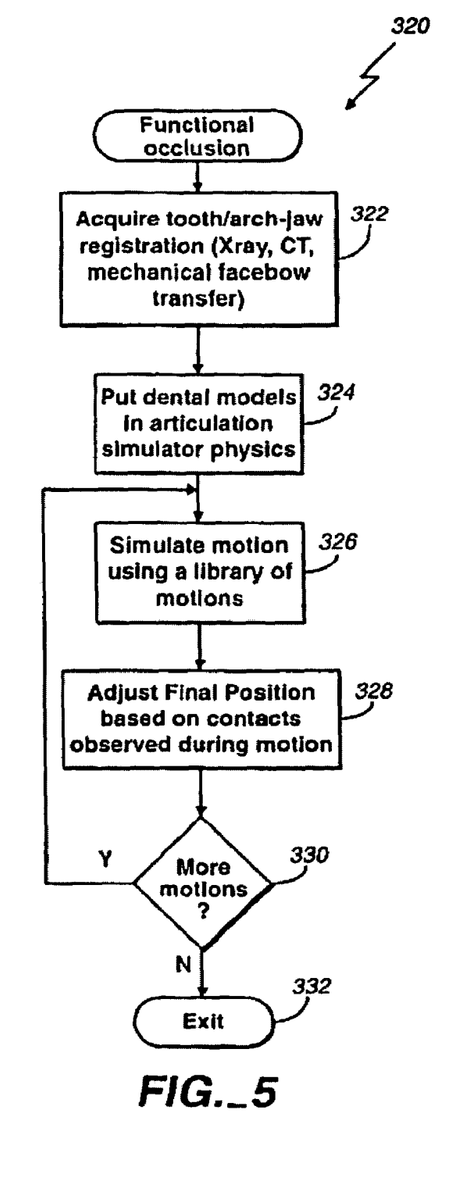
FIG. 5 is a flow chart illustrating a process for performing functional occlusion on the patient's teeth.

Turning now to FIG. 5, a process 320 for performing functional occlusion is shown. Functional occlusion is a process for determining how well the teeth fit together when the jaws move. The process 320 first acquires tooth/arch jaw registration. This may be done using conventional techniques such as X-ray, a computer tomography, or a mechanical device such as a face bow transfer.

After acquiring the registration information (322), the process 320 places digital dental models of the teeth in a digital articulation simulator (324). The articulation simulator allows a subset of jaw movements such as bite-movements to be simulated, as described below.

From 324, the process 320 simulates jaw motions (326). A simplified set of movement physics (kinematics) is applied to the dental models. The process 320 performs a simulation using a simplified set of interacting forces on the jaws 100 and 101 in relation to one another. The simplified physical simulation allows the system to focus on motions involving much contact between the jaws. The physical simulation allows the system to render realistic physically correct jaw movements when the jaws 100 and 101 come into contact with each other.

A range of simulated motion may be supplied using a library of motions. One typical motion supplied by the library is a protrusive motion where the lower jaw 101 is moved forward and backward to bring the front teeth on both jaws into contact with each other. Another motion is a lateral motion found in food chewing. The lateral motion involves moving the jaws 100 and 101 side to side. Other motions that may be supplied in the library include motions that are "tooth guided" where the path of the lower jaw 100 is guided by the teeth in contact with each other.

Next, the process 320 adjusts the final position based on contacts observed during the simulation of motions in 326 (328). The result of the simulation is analyzed, the position of each tooth can be adjusted if contacts associated with that tooth are deemed excessive.

Finally, based on the contact data generated, the process determines whether additional motion simulations need to be done. The motion simulation may be rerun until the contacts associated with each tooth are acceptable to the treating orthodontist. The tooth model manipulation process can be done subjectively, i.e., the user may simply reposition teeth in an aesthetically and/or therapeutically desired manner based on observations of the final position or based on the simulation of contacts. Alternatively, rules and algorithms may be used to assist the user in repositioning the teeth based on the contacts. If the simulation needs to be repeated, the process loops back to 326 (330). Alternatively, the process exits (332).

Figure 6:
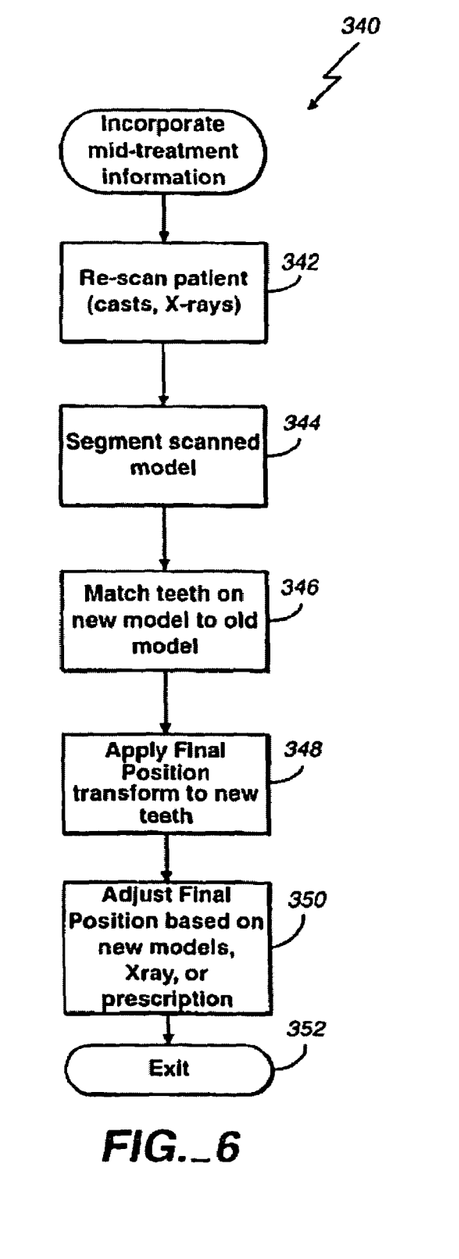
FIG. 6 is a flow chart illustrating an optional process for incorporating midtreatment information to the final placement of the patient's teeth.

FIG. 6 shows an optional process of 340 of incorporating midtreatment information to the final positioning process. First, a digital model incorporating dental information associated with the patient is generated from a scan of the patient's teeth (342). The scan may be performed using casts, X-rays or any of the conventional scanning methods.

Next, the digital model is segmented into one model for each tooth (344). Each tooth is then matched against a model associated with a prior scan developed at the beginning of the treatment plan (346). The matching process is based on matching corresponding points between the current scan and the prior scan of the teeth. In most cases, the teeth segmented from the current scan retain the shapes determined at the beginning of the treatment plan, and the matching process is easy because the models should be similar to each other.

A final position transform is then applied to the new teeth model (348). The final position and specification from the prior model is copied to the current model of the patient, and the final position is adjusted based on the new models, the new X-ray information or a new prescription (350). 350 basically involves rerunning the minimization process 300 (FIG. 4) described previously with the new information, which may be a slight change in the model, a change in the X-ray scan, or a change the prescription. Finally, the process 340 exits (352)

Figure 7:
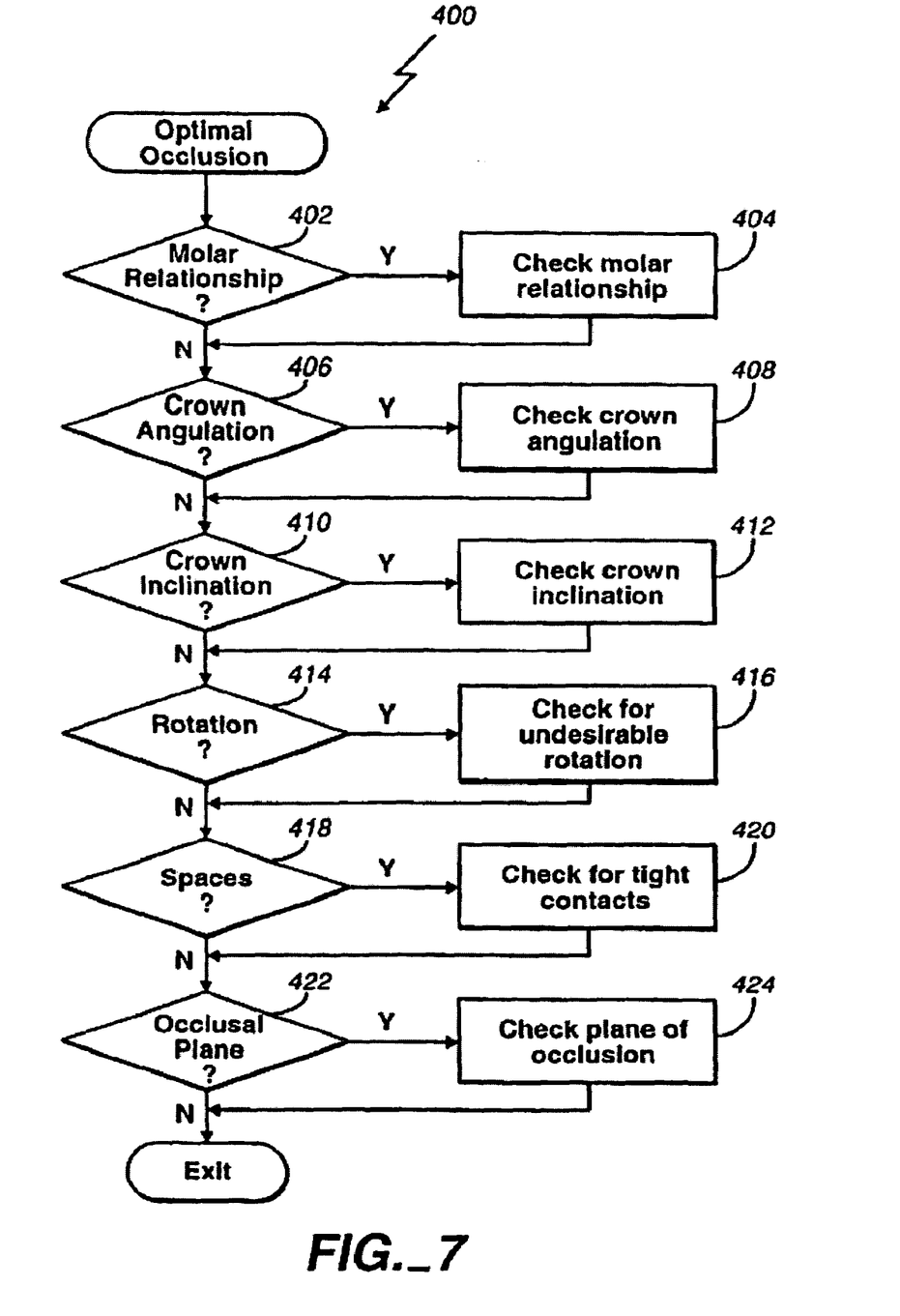
FIG. 7 is flow chart illustrating a process for optimizing occlusion based on one or more keys.

FIG. 7 is a flowchart of a process 400 for determining optimal occlusion in the teeth model. The process 400 optimizes the occlusion based on six characteristics (Six Keys) that were found to be consistently present in a collection of 120 casts of naturally optimal occlusion. The keys include a molar relationship key, a crown angulation key, a crown inclination key, teeth rotation key, teeth contact point key, and an occlusal plane key. The individual keys provide a complete set of indicators of optimal occlusion, can be judged from tangible landmarks, and can be judged from a facial and occlusal surfaces of the crowns, thus reducing the need for a lingual view for articulating paper to confirm occlusial interfacing. These keys are described in Lawrence F. Andrews, "The six keys to normal occlusion," Am. J. Orthod. Vol. 62, No. 3 pp. 296-309 (9/72) and in Chapter 3 of his book entitled Straight Wire—The Concept and Appliance (Published by L. A. Wells), the contents of which are incorporated by reference.

The Six Keys are interdependent elements of the structural system of optimal occlusion and are based on similarities in the patterns of angulation, inclination, shape, and relative size (facial prominence) of tooth types. As such, they serve as a base for evaluating occlusion. The Six Keys are used as treatment objectives for patients. The characteristics of the Six Keys are incorporated into the design of appliance 111 to enhance precision and consistency in treatment results.

The process 400 first checks whether optimization is to be done with respect to a molar relationship key (402). If so, the process 400 checks and applies an appropriate molar relationship (404). The molar relationship pertains to the occlusion and the interarch relationships of the teeth. 404 enforces the following seven requirements of the molar relationship key:

1. The mesiobuccal cusp of the permanent maxillary first molar occludes in the groove between the mesial and the middle buccal cusps of the permanent mandibular first molar.

2. The distal marginal ridge of the maxillary first molar occludes with the mesial marginal ridge of the mandibular second molar.

3. The mesiolingual cusp of the maxillary first molar occludes in the central fossa of the mandibular first molar.

4. The buccal cusps of the maxillary premolars have a cusp-embrasure relationship with the mandibular premolars.

5. The lingual cusps of the maxillary premolars have a cusp-fossa relationship with the mandibular premolars.

6. The maxillary canine has a cusp-embrasure relationship with the mandibular canine and first premolar. The tip of its cusp is slightly mesial to the embrasure.

7. The maxillary incisors overlap the mandibular incisors and the midlines of the arches match.

The cusp-groove and the marginal-ridge conditions of the molars, the cusp-embrasure relationship of the premolars and canines, and incisor overjet can be observed directly from the buccal perspective. A facial axis of the clinical crown (FACC) measurement is used to permit assessment of the lingual-cusp occlusion of the molars and premolars when these teeth are viewed from their mesiobuccal aspect, as explained below.

In 404, Interarch relationship of the posterior teeth of two dentitions can be the same, but the interfacing of the occlusal surfaces of the two dentitions may differ because of differing crown inclinations.

404 ensures that correct occlusal interfacing through correct interarch relationship, angulation, and crow inclination. Interarch relationship and angulation are best judged from the buccal perspective; crown inclination for posterior teeth is best judged from the dentition's mesiobuccal perspective. Judging posterior occlusion first from the buccal (for angulation and interarch relationship) then from the mesiobuccal (for inclination) provides a perspective that can be systematically described and quantified. Such information, along with other nonocclusal guidelines, are used in 404 to identify occlusal deviations.

404 includes occluding a first permanent molar with a second permanent molar. In such an occlusion, the first permanent molar has a distobuccal cusp with a distal surface, the second permanent molar has a mesiobuccal cusp with a mesial surface and the distal surface occludes with the mesial surface. The mesiobuccal cusp can occlude in a groove between mesial and middle cusps of the first permanent molar. The mesial surface can closely approach the distal surface. Moreover, where the teeth have canines and premolars, the canines and premolars have a cusp-embrasure relationship buccally and a cusp-fossa relationship lingually.

From 402 to 404, the process 400 checks whether the occlusion needs to be optimized with respect to a crown angulation key (406). If so, the occlusion is optimized with respect to the crown angulation key (408). Essentially, 408 ensures that all crowns should have a positive angulation, and all crowns of each tooth type should be similar in the amount of angulation. Further, the contact-area position for each tooth type should be similar. 408 determines a distal inclination of a gingival portion of the crown. The distal inclination may be constant within each tooth type. The angulation may be determined between the FACC and a line perpendicular to an occlusal plane. 408 may minimize the angulation, which may be positive or negative.

From 406 or 408, the process 400 checks whether the occlusion is to be optimized with respect to a crown inclination key (410). If so, the crown inclination optimization is performed (412). As they do in angulation, consistent patterns also prevail in crown inclination; the following three characteristics for individual teeth are analyzed in 412:

1. Most maxillary incisors have a positive inclination; mandibular incisors have a slightly negative inclination. In most of the optimal sample, the interincisal crown angle is less than 180° degree. The crowns of maxillary incisors are more positively inclined, relative to a line 90° degree to the occlusal plane, than the mandibular incisors are negatively inclined to the same line.

2. The inclinations of the maxillary incisor crowns are generally positive—the centrals more positive than the laterals. Canines and premolars are negative and quite similar. The inclinations of the maxillary first and second molars are also similar and negative, but slightly more negative than those of the canines and premolars. The molars are more negative because they are measured from the groove instead of from the prominent facial ridge, from which the canines and premolars are measured.

3. The inclinations of the mandibular crowns are progressively more negative from the incisors through the second molars.

In 412, the crown inclination can represent an angle formed by a line perpendicular to an occlusal plane and a line tangent to a bracket site. In this step, the crown inclination can be negative when measured from an upper canine through an upper second premolar. The crown inclination may become progressively more negative when measured from a lower canine through a lower second molar. The crown inclination may also be positioned between a line parallel and tangent to the FACC at its midpoint and a line perpendicular to an occlusal plane.

From 410 or 412, the process 400 checks whether the occlusion is to optimized using a rotation key (414). If so, the process 400 checks for undesirable rotations (416) and corrects the model so that tooth rotations are absent.

From 414 or 416, the process 400 then determines whether the occlusion needs to be optimized with respect to spacing (418). If so, the process 400 checks for tight contacts that is, no spaces should exist between teeth (420). 418 checks that contact points abut unless a discrepancy exists in mesiodistal crown diameter.

From 418 or 420, the process 400 then checks whether the occlusion is to be optimized with respect to an occlusal plane key (422). If so, the process 400 then optimizes the teeth model by analyzing the plane of occlusion (424). In 424, the depth of the curve of Spee ranges from a flat plane to a slightly concave surface. The plane can range between flat to curves of Spee. Moreover, the curve of Spee may be deep, slight, or reversed. From 422 or 424, the process 400 exits.

Figure 8:
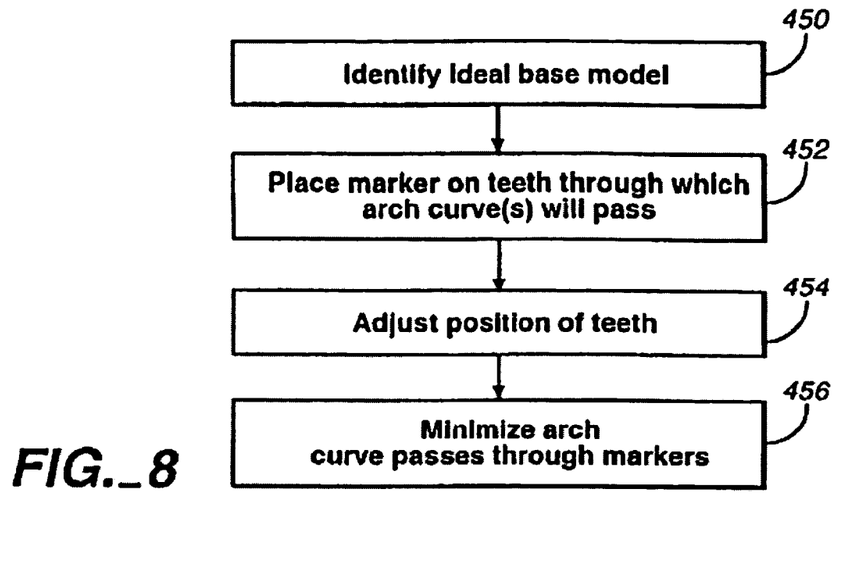
FIG. 8 is a flow chart illustrating a second process for performing functional occlusion on the patient's teeth.

FIG. 8 is a flow chart illustrating a second process for determining final position of the patient's teeth. The process of FIG. 8 identifies an ideal base model for the final position of the teeth that consists of an arch curve (450). This model can be selected from a suite of template models, derived from patients with ideal occlusion, or derived from patient under treatment (via the casts, X-rays, a prescription, or data about the patient from other sources). Next, the user of the software places and orients a marker on each tooth, through which the arch curve (or curves) is intended to pass (452). The curves can be designed so that they should pass through markers placed on the tooth's facial, lingual, or occlusal surface. Multiple arch curves can be used to make the specification of the final position more accurate. In 454, the position and orientation of the teeth are adjusted so that the arch curve passes through the marker on each tooth and the teeth do not overlap. Optionally, the teeth can be made to contact each other in this step. Next, where the teeth have multiple markers, the position and orientation of the tooth is set so that the arch curves pass as closely as possible through all markers on each tooth (456). In another implementation, the markers can be automatically placed and oriented on each tooth. The user can optionally adjust their position and orientation.

Figure 9:
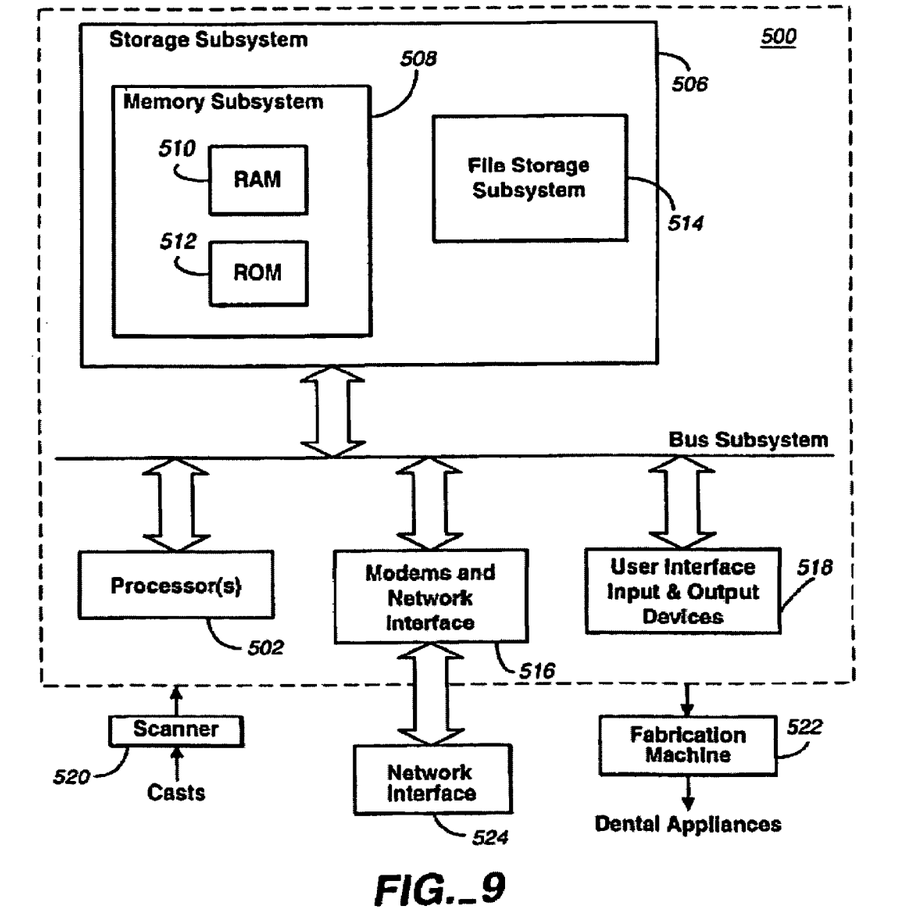
FIG. 9 is a block diagram illustrating a system for generating appliances in accordance with the present invention.

FIG. 9 is a simplified block diagram of a data processing system 500. Data processing system 500 typically includes at least one processor 502 which communicates with a number of peripheral devices over bus subsystem 504. These peripheral devices typically include a storage subsystem 506 (memory subsystem 508 and file storage subsystem 514), a set of user interface input and output devices 518, and an interface to outside networks 516, including the public switched telephone network. This interface is shown schematically as "Modems and Network Interface" block 516, and is coupled to corresponding interface devices in other data processing systems over communication network interface 524. Data processing system 500 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 506 maintains the basic programming and data constructs that provide the functionality of the present invention. The software modules discussed above are typically stored in storage subsystem 506. Storage subsystem 506 typically comprises memory subsystem 508 and file storage subsystem 514.

Memory subsystem 508 typically includes a number of memories including a main random access memory (RAM) 510 for storage of instructions and data during program execution and a read only memory (ROM) 512 in which fixed instructions are stored. In the case of Macintosh-compatible personal computers the ROM would include portions of the operating system; in the case of IBM-compatible personal computers, this would include the BIOS (basic input/output system).

File storage subsystem 514 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 504 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 520 is responsible for scanning casts of the patient's teeth obtained either from the patient or from an orthodontist and providing the scanned digital data set information to data processing system 500 for further processing. In a distributed environment, scanner 520 may be located at a remote location and communicate scanned digital data set information to data processing system 500 over network interface 524.

Fabrication machine 522 fabricates dental appliances based on intermediate and final data set information received from data processing system 500. In a distributed environment, fabrication machine 522 may be located at a remote location and receive data set information from data processing system 500 over network interface 524.

Figure 10A:
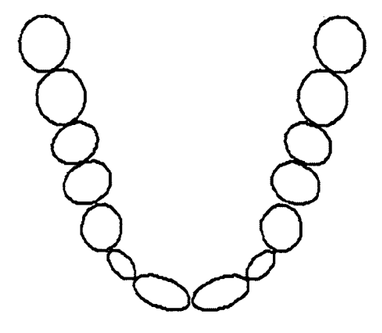
FIGS. 10A-10D is diagrams illustrating a process for temporally moving teeth.
Figure 10B:
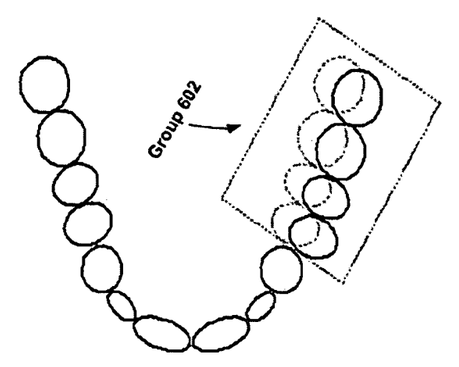
Figure 10C:
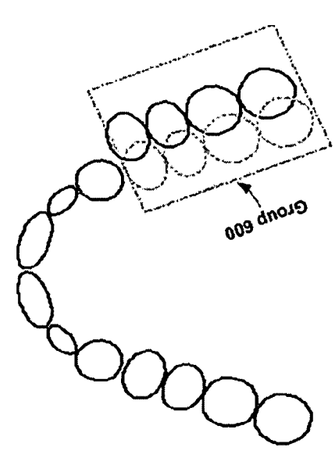
Figure 10D:
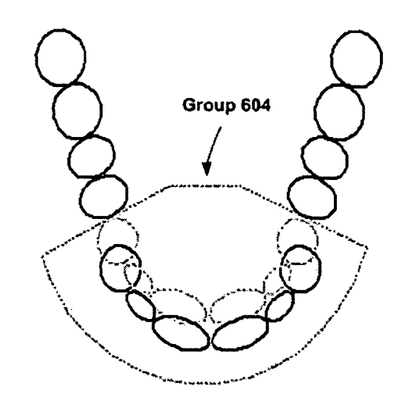

FIGS. 10A-10D illustrates an exemplary process for temporally moving teeth. In FIG. 10A, the teeth are shown at their rest position. In FIG. 10B, one or more teeth in group 600 are moved using a first dental appliance. Next, as shown in FIG. 10C, the teeth in group 600 are allowed to rest by relieving the force applied to them. In FIG. 10C, the teeth in a second group 602 are moved. Next, in FIG. 10D, the teeth in group 602 are allowed to rest by relieving the force applied to them while the teeth in a third group 604 are moved. In this manner, the process of FIGS. 10A-10D moves teeth by moving a first tooth or group of teeth; and then moves a second tooth or group of teeth while isolating the first tooth or group of teeth at a rest position.

The system to generate one or more appliances for a patient includes a processor; a display device coupled to the processor; a data storage device coupled to the processor; a scanner coupled to the processor for providing data to model the patient's masticatory system; means for moving a first tooth; means for moving a second tooth while isolating the first tooth at a rest position; and a dental appliance fabrication machine coupled to the processor for generating the appliances in accordance with the moved tooth and the isolated tooth.

Implementations of each of the above aspects may include one or more of the following. The second tooth can be moved for a first duration and immobilized for a second duration. The duration can be on an hourly basis, a daily basis, or a weekly basis. A plurality of appliances can be generated, wherein the appliances comprise polymeric shells having cavities and wherein the cavities of successive shells have different geometries shaped to receive and resiliently reposition the teeth from one arrangement to a successive arrangement. A first cavity isolates the first tooth at the rest position. A second cavity urges the second tooth to one of the successive position. The appliance can be replaced on an intra-day basis, daily basis, multi-day basis, intra-week basis, or weekly basis.

To keep the number of stages down, large numbers of teeth are moved at once in one appliance. Preferably, the same movement is distributed across two or more appliances to be worn successively in one period such as one day, for example. When one group of teeth moves, the other group is relieved of force/pressure on that group. Additionally, the system can move a first group of teeth; and move a second group of teeth while isolating the first group of teeth at a rest position. Each group can be contiguous teeth or can be non-contiguous teeth.

The staging of the appliance and teeth groupings is preferably done so moving one tooth or group of teeth does not cause contrary or reactive movement in the other tooth or group(s) of teeth. The appliances are identified in sequence to make it clear to the patient when or which order the intra-day stages should be worn. The markings can be printed on the appliances, the boxes containing the appliances can be marked with the sequence to be worn, or the boxes containing the appliances can be dispensed in a specific sequence of wear.

In one embodiment, relieving applied forces from intra-day stage to the next can be effected by using extra space in the dental appliance with or without pressure points. Another embodiment can engage or disengage the appliance for underlying attachments. In yet another embodiment for intra-day appliances, varying the thickness of the intra-day appliances can be used to permit relaxation since thicker appliances apply greater forces than thinner appliances.

Figure 11:
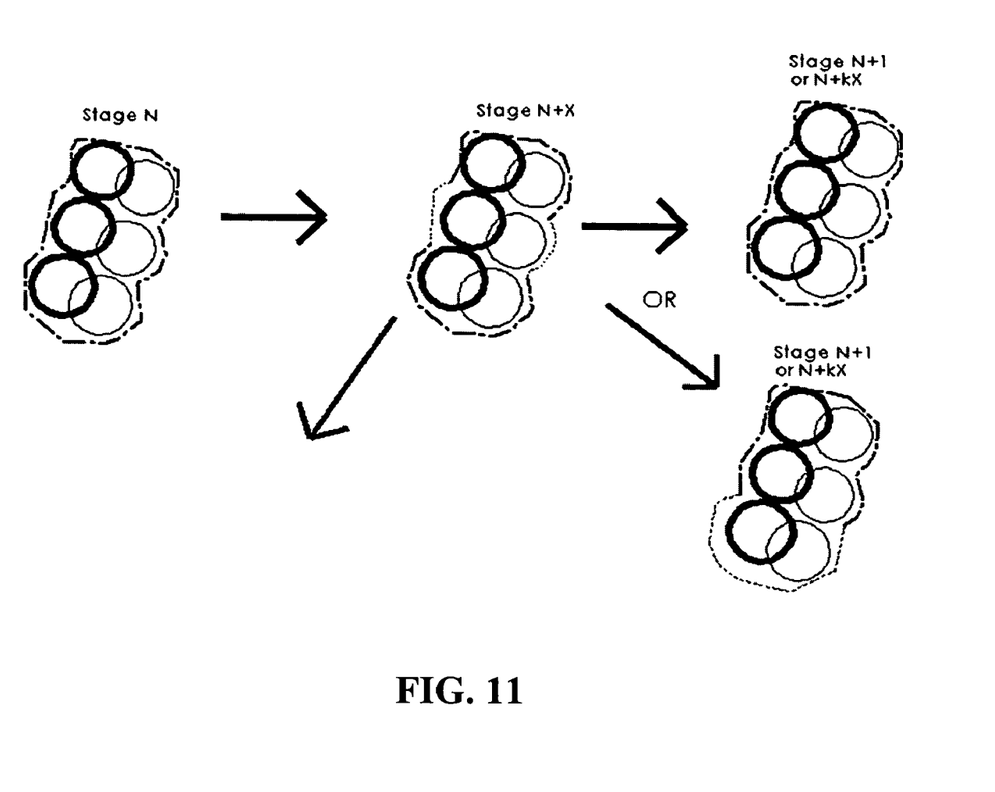
FIG. 11 is a diagram illustrating temporal movement of teeth.

FIG. 11 is a diagram illustrating temporal movement of teeth. In FIG. 11, each stage is manifested as one appliance. The appliance for each stage can be replaced on an intra-day basis, daily basis, multi-day basis, intra-week basis, weekly basis, biweekly basis, or any suitable period or duration. In this diagram, N is an arbitrary stage number, X may be a value up to the length of a stage or as short as a few hours, k is a multiple of for the value X, e.g. the patient would change appliances one or more times within a given period of time, for example a day.

At Stage N, heavy line circles represent current tooth positions, light lines represent intended positions, and dashed lines represent a dental appliance's deformation to cause motions. In Stage N+X, a dotted line represents that the appliance is not acting on the underlying tooth ('isolated' or 'neutralized' state). When a tooth or a group of teeth is isolated or neutralized, no force is applied to the tooth or group of teeth and it is allowed to 'REST'.

In one embodiment, a tooth or group of teeth is "isolated" or "neutralized" by creating space (volume) around the tooth such that, even when the appliance is at a maximum deflection for other teeth's movements, no undesirable contact exists between this tooth and the appliance. A number of methods can be used for space (volume) creation such as U.S. application Ser. No. 10/126,105, filed on Apr. 18, 2002, the content of which is incorporated by reference. It must be noted that despite being shown here in 2-D, the concept is applicable to 3-D with six degrees of freedom as well.

From Stage N+X, the treatment plan may go to Stage N+1 or N+kX where the isolated or neutralized tooth or teeth from previous stage(s) are re-activated to move. Alternatively, from Stage N+X, the treatment plan can go to Stage N+1 or N+kX where different tooth or teeth are isolated or neutralized while formerly isolated or neutralized teeth are re-activated and moved.

Other choices not depicted include but are not limited to:
additional teeth are neutralized
degree (amount) of re-activation is varied
order(s) of neutralization and re-activation is altered Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Further, while the invention has been shown and described with reference to an embodiment thereof, those skilled in the art will understand that the above and other changes in form and detail may be made without departing from the spirit and scope of the following claims.

What is claimed is:

1. A method for moving teeth, comprising:
moving at least one first tooth with a dental appliance having a number of cavities in which one or more teeth are positioned and wherein the at least one first tooth is positioned in one of the cavities; and
moving at least one second tooth while isolating the at least one first tooth by relieving the at least one first tooth of any applied force from the appliance or the second tooth, wherein relieving the force applied to the at least one first tooth is accomplished by creating space around the tooth and within the one of the cavities of the appliance, such that no force applying contact is made by the appliance or the second tooth.

2. The method of claim 1, wherein the at least one second tooth is moved for a first duration and immobilized for a second duration.

3. The method of claim 2, wherein the first duration is on an hourly basis, a daily basis, or a weekly basis.

4. The method of claim 1, comprising generating a plurality of appliances based on the moving of the at least one first tooth and the at least one second tooth, wherein the appliances comprise polymeric shells having cavities and wherein the cavities of successive shells have different geometries shaped to receive and resiliently reposition the at least one first and second teeth from one arrangement to a successive arrangement.

5. The method of claim 4, wherein a first cavity isolates the at least one first tooth at the rest position.

6. The method of claim 4, wherein a second cavity urges the at least one second tooth to the successive arrangement.

7. The method of claim 4, further comprising replacing an appliance on an intra-day basis.

8. The method of claim 4, further comprising replacing an appliance on a daily basis.

9. The method of claim 4, further comprising replacing an appliance on a multi-day basis.

10. The method of claim 4, further comprising replacing an appliance on an intra-week basis.

11. The method of claim 4, further comprising replacing an appliance on a weekly basis.

12. The method of claim 1, wherein the at least one first tooth is a group of contiguous teeth.

13. the method of claim 1, wherein the at least one first tooth is a group of noncontiguous teeth.

14. The method of claim 1, wherein the at least one second tooth is a group of contiguous teeth.

15. The method of claim 1, wherein the at least one second tooth includes a group of noncontiguous teeth.

* * * * *